United States Patent
Greter et al.

(10) Patent No.: US 8,840,593 B2
(45) Date of Patent: Sep. 23, 2014

(54) DISCHARGE APPARATUS HAVING COMPRESSED GAS SUPPORT

(75) Inventors: Andy Greter, Baar (CH); William Brem, Muri (CH)

(73) Assignee: Medmix Systems AG, Rotkreuz (CH)

( * ) Notice: Subject to any disclaimer, the term of this patent is extended or adjusted under 35 U.S.C. 154(b) by 698 days.

(21) Appl. No.: 13/143,961

(22) PCT Filed: Dec. 17, 2009

(86) PCT No.: PCT/CH2009/000400
§ 371 (c)(1),
(2), (4) Date: Jul. 11, 2011

(87) PCT Pub. No.: WO2010/081244
PCT Pub. Date: Jul. 22, 2010

(65) Prior Publication Data
US 2011/0278375 A1    Nov. 17, 2011

(30) Foreign Application Priority Data

Jan. 13, 2009 (CH) .................................... 0045/09

(51) Int. Cl.
| | |
|---|---|
| *A61M 5/315* | (2006.01) |
| *A62C 5/02* | (2006.01) |
| *B05B 7/26* | (2006.01) |
| *B05B 7/12* | (2006.01) |
| *A61M 5/00* | (2006.01) |
| *B05B 7/24* | (2006.01) |
| *B05C 17/005* | (2006.01) |
| *A61B 17/00* | (2006.01) |

(52) U.S. Cl.
CPC ......... *A61B 17/00491* (2013.01); *B05B 7/2416* (2013.01); *B05B 7/12* (2013.01); *B05C 17/00553* (2013.01); *A61B 2017/00495* (2013.01); *B05C 17/00593* (2013.01)
USPC ........... 604/236; 604/203; 604/207; 604/258; 222/145; 239/310; 239/407

(58) Field of Classification Search
CPC .......... A61M 5/315; A61M 5/00; A62C 5/02; B05B 7/12
USPC ......... 239/294, 300, 301, 302, 303, 310, 311, 239/337, 375, 398, 407, 525, 526; 606/93; 604/191, 82, 272, 225, 8.9, 91, 35, 604/218, 56, 83, 85, 187, 236, 238, 249, 604/208, 266, 269, 94; 222/137, 127, 142, 222/145.1
See application file for complete search history.

(56) References Cited

U.S. PATENT DOCUMENTS 4,645,496 A    2/1987   Oscarsson
(Continued)

FOREIGN PATENT DOCUMENTS

WO    95/31138 A1    11/1995

*Primary Examiner* — Justin Jonaitis
(74) *Attorney, Agent, or Firm* — Sughrue Mion, PLLC (57) ABSTRACT

A discharge apparatus for discharging a product having compressed gas support comprises a container (1) having a discharge opening (12) and a pressure element (2), which is mounted displaceably in the container (1). A counterpressure element (13) is provided on the container (1) and is used to advance the pressure element (2) into the container in order to absorb a developing counterpressure when pressure is applied onto the pressure element (2). A compressed gas device (5, 7, 8) dispenses compressed gas in the region of the discharge opening (12), and comprises a valve (6) and a valve actuating device (14) to control the compressed gas dispensing. The actuating device (14) is provided on the counterpressure element (13) to ensure that when discharging the product from the container, at the same time the compressed gas device can be actuated by applying pressure onto the pressure element, whereby compressed gas exits the discharge opening at the same time as the fluid product.

13 Claims, 5 Drawing Sheets

(56) References Cited

U.S. PATENT DOCUMENTS

| | | | |
|---|---|---|---|
| 5,334,163 A * | 8/1994 | Sinnett | 604/236 |
| 5,582,596 A * | 12/1996 | Fukunaga et al. | 604/191 |
| 6,673,093 B1 * | 1/2004 | Sawhney | 606/214 |
| 8,534,575 B2 * | 9/2013 | Brem | 239/422 |
| 2002/0165483 A1 * | 11/2002 | Miller et al. | 604/82 |
| 2006/0191962 A1 * | 8/2006 | Redl et al. | 222/386 |

* cited by examiner

DISCHARGE APPARATUS HAVING COMPRESSED GAS SUPPORT

CROSS REFERENCE TO RELATED APPLICATIONS

This application is a National Stage of International Application No. PCT/CH2009/000400, filed Dec.17, 2009, which claims priority from Swiss Patent Application No. 00045/09, filed Jan. 13, 2009, the contents of all of which are incorporated herein by reference in their entirety.

TECHNICAL FIELD

The present invention relates to a discharge apparatus having compressed gas support for spraying a product onto an application surface, in particular for spraying two-component products onto a treatment surface within the context of a medical application. Furthermore, the invention relates to a method for discharging a product from a discharge apparatus of this type.

PRIOR ART

For various applications, a product which is generally present in fluid form has to be stored in a container, for example a syringe, and, upon use, applied to a surface by spraying. For example, tissue adhesives, for example Fibrin or Thrombin, are stored in the form of separate components in a double syringe and can be sprayed onto a tissue surface with the aid of a discharge apparatus which has compressed gas support. In the process, the two adhesive components are mixed with each other in the spray produced by the compressed gas device outside a spray nozzle of the discharge apparatus, in order to prevent the spray nozzle from clogging by the adhesive. In this case, spraying onto the tissue surface may be interrupted without clogging of the spray nozzle. Adhesives of this type are used, for example, for wound treatment or for stopping bleeding.

A discharge apparatus having compressed gas support is known, for example, from US 2002/0165483 A1. This document provides a double chamber syringe with different components of an adhesive in each chamber, the chambers having a common pressure plunger for discharging the components from a discharge opening in the syringe. The syringe is attached to a gas source by means of a holder or is connected by means of a line to a gas source which provides compressed gas in the region of the discharge opening in the syringe. Furthermore, a regulating valve which regulates the release of compressed gas from the gas source is provided on the holder for the syringe. A compressed gas line leads from the compressed gas source to the region of the discharge opening for the two components on the syringe such that, as the components emerge, the compressed gas can act directly on the components. When said discharge apparatus is used, a gas pressure is first generated at the discharge opening by means of the regulating valve and, subsequently, the components are discharged from the chambers of the double syringe by advancing the pressure plunger. Directly after emerging, said components enter the compressed gas stream and are therefore atomized and mixed with one another. The compressed gas stream subsequently transports the mixture onto the application surface. If the spraying is interrupted or the syringe has been emptied, the exertion of the pressure on the pressure piston is interrupted and the gas stream can be shut off by means of the regulating valve.

US 2006/0191962 A1 shows a further discharge apparatus having compressed gas support, in which the discharge apparatus in the form of a double syringe having a double pressure plunger is connected to a stationary compressed gas source. A first line leads from the compressed gas source to the discharge opening in the syringe such that components emerging from the opening can be atomized. A second line leads from the compressed gas source to a head part of the double pressure plunger, the push-on region of said head part having an opening from which a gas stream can emerge, said gas stream being guided through the second line. The housing of the double syringe containing the syringe chambers has counter-pressure surfaces at which the syringe is held with the fingers while the double pressure plunger is pressed into the syringe by means of the thumb. In this case, the opening in the pressure region of the double pressure plunger is closed and the gas stream is prevented from emerging. As a result, a signal is generated in the compressed gas source, the signal triggering the production of a gas stream in the first line to the discharge opening of the discharge apparatus such that the components which are discharged by the pressure being applied to the double pressure plunger are atomized by the gas stream.

In the case of the discharge apparatus according to US 2002/0165483 A1, a plurality of actions in succession are necessary in order to produce the discharging of the components at the discharge apparatus and a gas stream at the discharge opening of the discharge apparatus simultaneously. As an alternative, it would be possible to operate the discharge apparatus with two hands in order to be able simultaneously to operate the regulating valve and the pressure plunger. In contrast, in the case of the discharge apparatus according to US 2006/0191962 A1, two different, independent compressed gas lines are necessary in order to be able to produce a gas stream at the discharge opening at the same time as the components are being discharged from the double syringe. The gas stream cannot be regulated here.

U.S. Pat. No. 5,582,596 discloses, in FIGS. 9-12, a discharge apparatus in which a double syringe is held in a gun-like applicator. When a lever, which is configured in the manner of a gun trigger, is actuated, on the one hand a spring-loaded plunger rod is released, pressing the plungers of the double syringe forward in order to discharge the substances from the double syringe. On the other hand, a compressed gas valve is opened by the actuation of the lever in order to produce a gas stream at the output of the applicator and, as a result, to spray the discharged substances. While said apparatus is simple to operate, it does not permit precise control of the quantity of substances discharged during the spraying operation. In addition, said apparatus is of relatively complicated construction and requires a large amount of space.

A gun-like discharge apparatus for spraying substances and having compressed gas support is also known from WO 95/31138. This apparatus also requires a large amount of space.

SUMMARY OF THE INVENTION

It is an object of the present invention to provide a discharge apparatus for discharging a product and having compressed gas support, which is simple to handle, requires only a few working steps to discharge a product, permits low consumption of compressed gas and enables the discharge apparatus to be constructed compactly.

A discharge apparatus for discharging a product and having compressed gas support comprises a container for the fluid product, which container has a discharge opening and a pressure element which is mounted displaceably in the container in order to be able to discharge the product from the container through the discharge opening. The container can be provided, for example, in the form of a conventional syringe, in particular in the form of a double chamber syringe. The product can be present as an aqueous solution or as a viscous product. Furthermore, the product can consist of a plurality of separate components which are provided, for example, in one chamber each of a double chamber syringe. It is possible to first of all mix the components of the product within the container and only then to discharge the product through the discharge opening. However, different components are preferably mixed outside the discharge apparatus by atomizing by means of a compressed gas. The pressure element used may be, for example, a pressure plunger which is connected to a stopper in the container or a stopper in a component chamber and can advance said stopper in the container in order thereby to reduce the size of the container volume and to press the product out through the discharge opening. The container is preferably of elongate design and has the discharge opening at one end and, at the opposite end, the pressure element can be pressed into the container.

Furthermore, a counterpressure element which, when pressure is applied to the pressure element to advance the pressure element into the container, serves to absorb the counterpressure arising in the process, is arranged on the container. The counterpressure element is connected fixedly to the container or can be attached removably to the container. If the counterpressure element is attached to the container, said counterpressure element is stationary relative to the container. In order to discharge the product, the container can be grasped at the counterpressure element, for example with the fingers, and the pressure element can be pressed into the container by means of the thumb, with it being possible for the container to be held in a fixed position at the counterpressure element with the fingers. For this purpose, the counterpressure element has one or more counterpressure surfaces which are preferably provided on the side of or on two opposite sides of the container.

Furthermore, the discharge apparatus according to the invention has a compressed gas device for dispensing compressed gas in the region of the discharge opening and an actuating device for actuating a valve for controlling the dispensing of compressed gas from the compressed gas device. The compressed gas device can be provided as a conventional gas cartridge or as a spray can in handy form or else as a positionally fixed compressed gas generator. The compressed gas can be guided by means of a supply line to the valve and from the valve into the region of the discharge opening by means of a dispensing line. In the region of the discharge opening, the dispensing line can be connected to a conventional spray head which can be placed onto the discharge opening of the discharge device in order to be able to produce a suitable gas flow around the discharge opening. Spray heads of this type are known from the prior art. In this case, the discharge opening for discharging the product from the container is provided by the discharge opening in the spray head. The spray head is arranged fixedly relative to the container and can therefore be theoretically considered part of the container. The valve can be brought by means of the actuating device from a closed valve position, in which a gas stream is not guided into the dispensing line, into an at least partially open valve position, in which a gas stream from the compressed gas device is conducted through the valve into the dispensing line and to the discharge opening.

According to the present invention, the actuating device for actuating the valve of the compressed gas device is provided on the counterpressure element which is arranged on the container for the fluid product.

According to the invention, at the same time as the exertion of pressure required for discharging the fluid product from the container, the valve of the compressed gas device can therefore also be opened and therefore a stream of compressed gas is generated in the region of the discharge opening in the container. The stream of compressed gas is therefore produced and the fluid product discharged at the discharge opening by the same action. It is not required to produce the gas stream through a valve opening in a first step and subsequently, in a second step, to discharge the product from the container while the gas is already flowing out. As a result, the consumption of compressed gas can be reduced, and the handling of the discharge apparatus is simplified. The stream of compressed gas is controlled within the line section thereof extending from the compressed gas source to the discharge opening on the container. The discharge device according to the invention therefore requires only few components and has little susceptibility to faults.

According to one embodiment of the invention, the valve can be provided as a shut-off valve which is formed, for example, by a valve inner drum and a valve outer drum which are arranged concentrically with respect to each other and are rotatable with respect to each other. The compressed gas supply line can open out into an opening in the circumferential wall of the valve outer drum and can therefore introduce the compressed gas into the interior of the drum. The dispensing line can open out at one end from the valve inner drum, the valve inner drum having, in the circumferential wall thereof, an opening which is congruent with the opening of the outer drum in a certain rotational position of the inner and outer drums with respect to each other. If the two openings come to lie one above the other, the compressed gas can flow out of the compressed gas source through the supply line and the two openings into the valve inner drum and from there into the dispensing line. If the two drums are in a rotational position in which the two openings are not congruent, the outer wall of the valve inner drum acts as a shut-off member of the shut-off valve.

The actuating device on the counterpressure element can be provided, for example, in the form of at least one lever for actuating the valve. The axis of rotation of the at least one lever is preferably substantially perpendicular to the advancing direction of the pressure element, and the lever arm of the lever preferably likewise extends substantially perpendicularly to the advancing direction. The lever surface along the longitudinal side of the lever, i.e. the surface which is formed by the lever arm, preferably corresponds to the counterpressure surface which is formed on the counterpressure element and on which the counterpressure acts upon advancing of the pressure element into the container. Accordingly, according to the present invention, at the same time as a pressure is exerted on the pressure and counterpressure elements, a pressure is advantageously also exerted on the lever surface, or on the lever arm, of the actuating device, as a result of which the lever can be pivoted from an inoperative position into an actuating position. The valve is brought in the process from a closed valve position, which corresponds to an inoperative position of the discharge apparatus, into an at least partially open valve position, which corresponds to the actuating position of the discharge apparatus, such that a gas stream is guided to the discharge opening. For this purpose, the lever is preferably connected directly to the valve inner drum such that the valve inner drum is actuated together with the lever and is therefore rotated within the valve outer drum as soon as a pressure is exerted on the counterpressure element. In this case, the valve outer drum can remain at rest relative to the container. As an alternative, it would, of course, be possible to connect the lever to the valve outer drum and to arrange the valve inner drum in a stationary manner with respect to the container. In this embodiment, the axis of the valve inner drum and valve outer drum therefore corresponds to the axis of rotation of the lever.

In one embodiment of the invention, the actuating device can be formed, for example, by two levers which are arranged parallel to each other and are provided on two opposite sides, for example on the left and right, of the container. The two levers preferably have a common axis of rotation.

In a further embodiment, it is also possible that the counterpressure surface of the counterpressure element does not correspond directly to the lever surface along the lever arm but rather the counterpressure surface is provided in the region of the axis of rotation of the lever. In this variant embodiment, in order to discharge a fluid product from the container, the thumb can act on the pressure element and a central region of a finger can act on the counterpressure surface in the region of the axis of rotation of the lever. A pressure can therefore be built up between the pressure element and the counterpressure element without a force acting directly on the lever. The lever can then be moved in a metered manner by the tip of the finger while the central region of the fingers absorbs the counterpressure caused by the advancing of the pressure element. The supply of compressed gas at the discharge opening can therefore be regulated independently of the pressure which is necessary for discharging the fluid product. In this case, the regulation can take place by the openings on the valve outer drum and the valve inner drum only being brought partially to overlap. In this case, the flow of compressed gas through the valve is proportional to the amount by which the two openings overlap.

In the described embodiment, the valve of the compressed gas device is described as a rotary valve or corner valve. In principle, however, it is also possible to use other valves, for example a lifting valve, for a discharge apparatus according to the present invention. In such a case, the valve does not have to be actuated by a rotational movement as is carried out in the previous example by means of a lever. Use may be made of other actuating mechanisms, for example parallel movements, which can likewise be produced with the building up of the pressure between the pressure element and counterpressure element. A parallel movement of this type preferably runs counter to the advancing direction of the pressure element.

The actuating device can be prestressed by means of a spring in such a manner that the valve is in a closed position in the inoperative position of the actuating device and, when the actuating device is actuated, can be moved counter to the force of a spring into an actuating position in which said valve is brought into an at least partially open position. It is ensured by the prestressing by means of the spring that the valve is closed in the inoperative position of the actuating device and is brought into an open position only when the discharge apparatus is actuated by a movement of the actuating device counter to the force of the spring. The spring is provided, for example, as a simple spiral spring in the region of the axis of rotation of a lever which serves as the actuating device.

In the present invention, the subassembly which comprises the counterpressure element, the actuating device, the valve and optionally also the supply and dispensing lines is designed to be usable repeatedly. The subassembly can be removed as a whole from a container and placed onto a new container. For this purpose, for example, a clipping or latching device can be provided, with which the subassembly can be snapped onto the container. In the process, for example, a lever of the actuating device comes to lie laterally on the container, the lever arm running perpendicularly to the advancing direction of the pressure element in the container. Latching devices or stops for supporting the subassembly or the clipping or latching device can be provided on the container such that the subassembly can be positioned precisely relative to the container and, after being placed onto the container, is held immovably relative thereto. The dispensing line can be connected in a simple manner to a spray head which is placed onto the discharge opening of the container. A compressed gas container can be connected to the supply line, for example by means of a Luer connection. The compressed gas container can thereby be interchanged without great effort.

According to another embodiment of the present invention, the actuating device can be provided next to a counterpressure surface of a counterpressure element mounted on the housing. For example, the container can be grasped in such a manner that a thumb comes to lie on the pressure element and the ring and middle fingers each rest on a counterpressure surface of the counterpressure element. With the index finger, the actuating device which is arranged next to the counterpressure surface can then be actuated independently of pressure being exerted on the pressure element of the container. If the actuating device has a lever, said lever can be arranged movably next to the counterpressure surface mounted on the housing. This variant embodiment also does not require any different actions in order to initially build up a stream of compressed gas and subsequently to discharge the product from the container. The discharging of the product and the actuation of the compressed gas device can be carried out from the same holding position of the discharging apparatus. However, the exertion of a force on the counterpressure surface and on the actuating device can take place independently of each other.

An apparatus of this type can be employed not only for spraying medicinal wound adhesives or tissue adhesives but also in other, in particular nonmedicinal, applications. Although the invention can therefore be employed in therapeutic or surgical applications, it is in no way restricted to such applications.

In a method (operating method) for discharging a product from a discharge apparatus having compressed gas support, as has been described above, the discharge apparatus is grasped according to the invention with one hand, wherein the thumb comes to lie on the pressure element and at least one finger comes to lie on the counterpressure element. After the discharge apparatus has been grasped, the pressure element and the counterpressure element are compressed by pressing the thumb and the at least one finger together. The pressure element is simultaneously advanced into the container and the valve can be opened by the actuating device being actuated. The actuating device can be operated by the same finger as the counterpressure element or else by another finger.

BRIEF DESCRIPTION OF THE DRAWINGS

Preferred embodiments of the invention are illustrated below with reference to the drawings which serve merely for explanation and should not be interpreted as being limiting. Features of the invention that become obvious from the drawings should be considered individually and in every combination as belonging to the disclosure of the invention. In the drawing.

DESCRIPTION OF PREFERRED EMBODIMENTS

Figure 1:
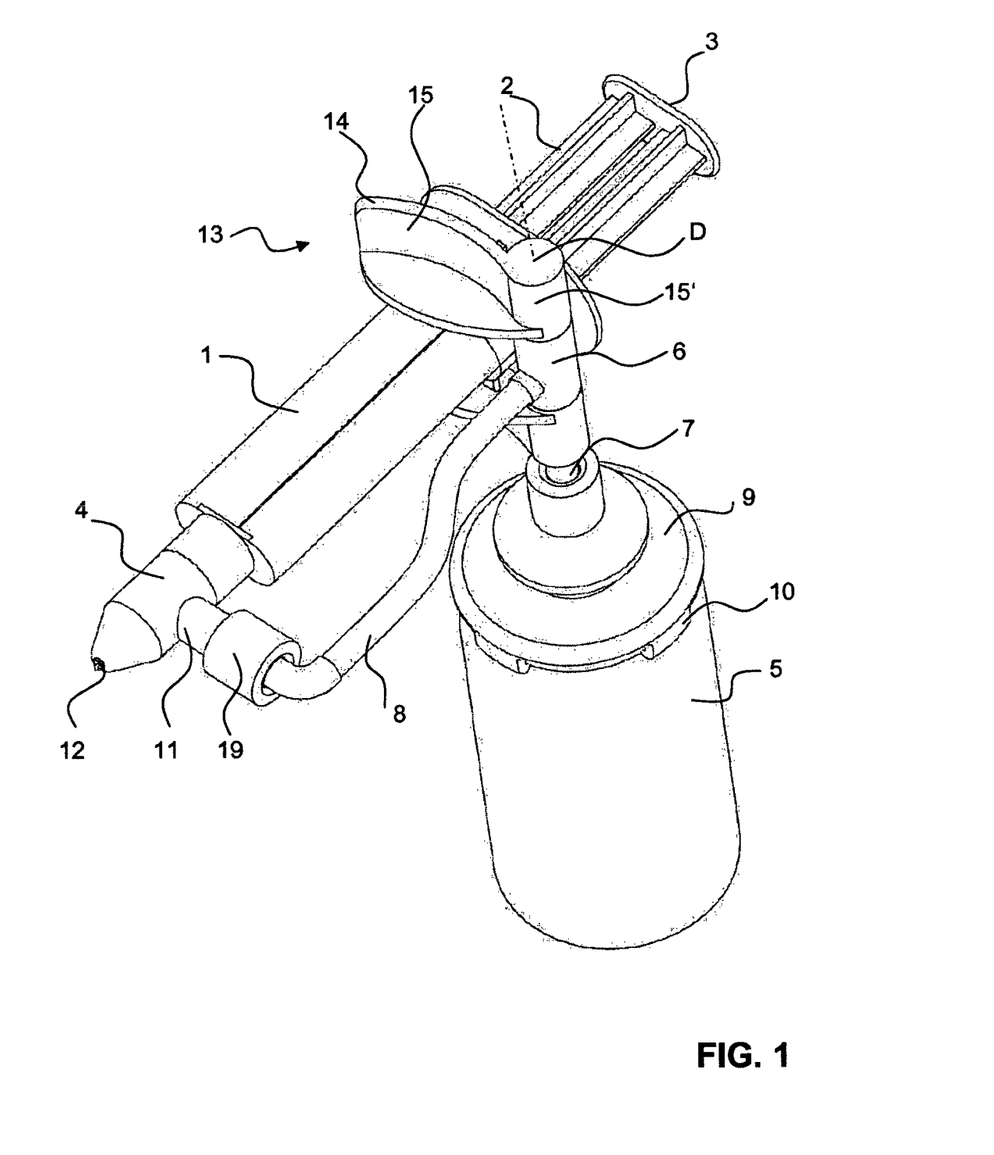
FIG. 1 shows a perspective illustration of a discharge apparatus according to the present invention.

FIG. 1 shows an embodiment of a discharge apparatus having compressed gas support according to the present invention. The discharge apparatus comprises a container 1 in the form of a double syringe with two chambers for different components of a product. A pressure element 2 which is designed as a double plunger, the two plunger rods of which each protrude into one of the chambers of the double syringe, is formed at one end of the double syringe. The pressure element is movable relative to the container, or the chambers, in such a manner that said pressure element can be pushed into the chambers by pressure being exerted on a pressure surface 3 on the pressure element, in order to reduce the volume of the chambers. On that side of the container which is opposite the double plunger, a spray nozzle 4 is arranged over a discharge opening of the container. The spray nozzle 4 is removable and can be fastened to the container, for example, by means of a bayonet connection. The spray nozzle 4 has one or more discharge openings 12 through which the product, or the components of the product, is or are discharged from the discharge apparatus.

A compressed gas device is provided which comprises a compressed gas source 5 in the form of a gas cartridge, a valve 6, a supply line 7 between the compressed gas source and the valve, and a dispensing line 8, which is guided from the valve 6 to the spray nozzle 4. The compressed gas source 5 is inserted, for example snapped, into a holder 9, a connection being produced between the compressed gas and the supply line 7. In order to fasten the compressed gas source 5 to the holder 9, it is possible, for example, to provide snap-on arms 10 which engage behind a border or an edge on the compressed gas source. In this case, a valve on the compressed gas source 5 is activated by pressing the holder 9 on and therefore producing the compressed gas connection. The dispensing line 8 can be fastened removably to a gas inlet 11 of the spray nozzle 4 by means of a plug-in connection. However, in the present example, said dispensing line is attached to the gas inlet 11 by a cap nut 19. Compressed gas from the gas source 5 can therefore be conducted via the supply line 7, the valve 6, the dispensing line 8, the gas inlet 11 and internal lines in the spray nozzle 4 into the region of the discharge opening 12.

A counterpressure element 13 is plugged onto the container at that end of the container 1 from which the pressure element 2 projects. The counterpressure element 13 is fastened to the container in such a manner that it is fixed relative to the container in the plugged-on state. However, the plug-in connection is designed to be releasable, as is explained further on. The counterpressure element 13 serves to provide a counterpressure surface in order to be able to absorb the counterpressure which arises when pressure is applied to the pressure element for advancing into the container. In the exemplary embodiment shown, the counterpressure element 13 has a lever 14 with a lever arm which is mounted rotatably or pivotably about an axis of rotation D. The lever 14 has a counterpressure surface 15 which extends along the lever arm between the axis of rotation and the opposite end point of the lever arm. As an alternative, that region of the lever which is arranged around the axis of rotation can be considered to be the counterpressure surface 15'. The lever 14 is pivotable about the axis of rotation D and can actuate the valve 6 by means of the pivoting movement, i.e. can close, partially open or completely open the valve. The lever 14 therefore acts on the counterpressure element 13 as an actuating device with which the compressed gas device can be operated.

In the embodiment shown, the valve 6, the axis of rotation of the lever 14 and the supply line 7 are aligned along an axis. In principle, however, it is also possible to use a compressed gas source which is stationary and can guide compressed gas to the valve by means of a flexibly designed, long supply line. The axis of rotation D for the valve and the lever runs perpendicularly to the advancing direction in which the pressure element 2 is advanced into the chambers of the container 1. The counterpressure surface 15 of the lever arm is aligned approximately perpendicularly to the advancing direction and preferably perpendicularly to the axis of rotation. The alignment of the counterpressure surface can vary about said perpendicular position depending on the actuating position of the lever 14.

Figure 2:
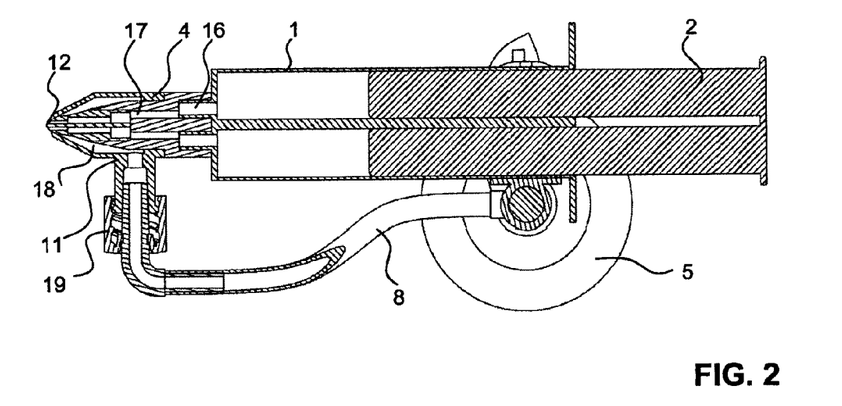
FIG. 2 shows a longitudinal section through a discharge apparatus according to FIG. 1.

FIG. 2 shows a longitudinal section through the discharge apparatus according to FIG. 1. The pressure element 2 is pushed into the chambers as far as half of the chamber volumes of the container 1. The pressure element 2 tightly closes off the chambers in the manner of a stopper such that, when the pressure element 2 is advanced into the container 1, the components in the chambers can be dispensed through openings 16 into the spray nozzle 4. The spray nozzle 4 has component lines and compressed gas lines 18 which open out in the region of the discharge opening 12 from the spray nozzle. The dispensing line 8 is fastened to the gas inlet 11 of the spray nozzle 4 by means of the cap nut 19.

Upon actuation according to the invention of the discharge apparatus, the components are conveyed out of the container 1 through the component lines 17 to the discharge opening 12 and at the same time a stream of compressed gas from the compressed gas device is conveyed through the dispensing line 8, the gas inlet and the compressed gas lines 18 to the discharge opening 12. The compressed gas which emerges at the discharge opening 12 can atomize the components which likewise emerge at the discharge opening 12 such that the desired adhesive mixture is produced and the mixture can be transported by means of the gas stream to an application surface.

Figure 3A:
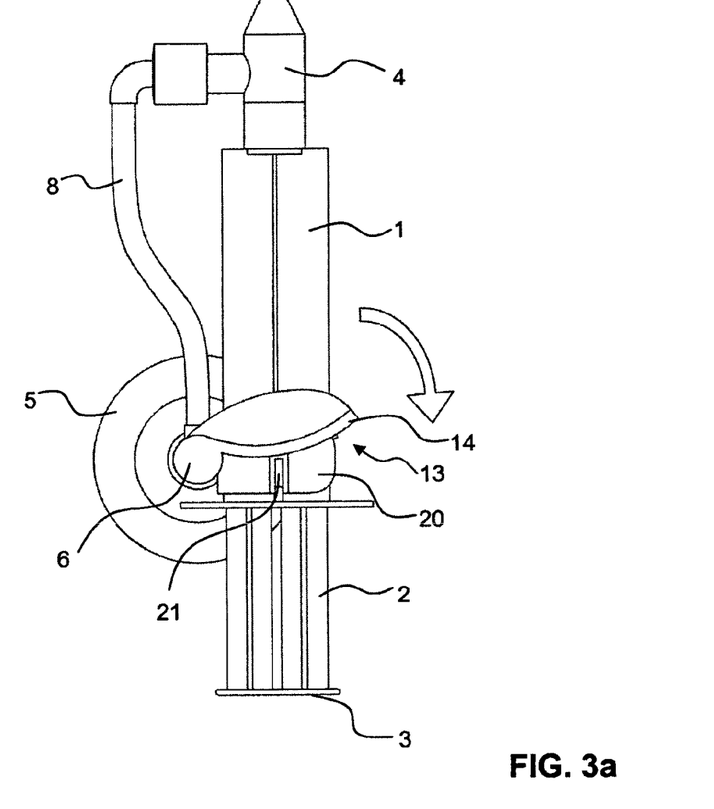
FIG. 3a shows a schematic illustration of a discharge apparatus according to the invention in a position with a closed valve.

FIG. 3a shows the discharge apparatus in a starting position, or inoperative position, before components are discharged. The valve 6 is in a closed position in which compressed gas cannot be conducted into the discharge line 8. The lever 14 is in a first position, the inoperative position. In said position, the lever is pivoted away from the pressure element 2, or the pressure surface 3 and the border of the container, i.e. said lever is at a greater distance from the end region of the container 1 than in an actuating position which is described in FIG. 4a. The counterpressure element 13 is placed onto the container 1 such that the axis of rotation of the lever comes to lie to the side of the container and perpendicularly to the advancing direction of the pressure element 2. For the fastening to the container 1, the counterpressure element has a snap-on clip 20 with which the counterpressure element can be fastened on the container. An elongate projection 21 which serves as a spacer between the snap-on clip 20 and the housing 1 is provided on the outside of the container 1.

Figure 3B:
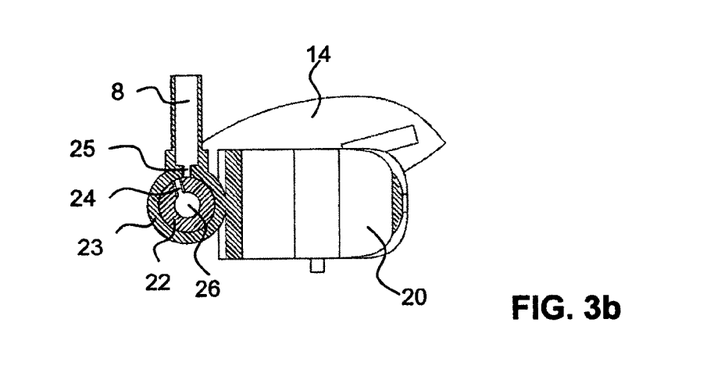
FIG. 3b shows a detailed longitudinal section through a valve of the discharge apparatus according to FIG. 3a, FIG. 4a shows a schematic illustration of a discharge apparatus according to the invention in a position with the valve open.

FIG. 3b shows a detailed section through the counterpressure element 13, in which the valve 6 which is coupled to the lever 14 can be seen in an inside view. The valve is designed as a shut-off valve and comprises a valve inner drum 22 and a valve outer drum 23. The drums 22 and 23 are mounted concentrically one inside the other and are rotatable in relation to each other. The valve outer drum 23 is arranged fixedly at the snap-on clip 20 of the counterpressure element 13 and is therefore immovable relative to the container 1 in the functionally ready state of the discharge apparatus. The valve inner drum 22 is coupled to the lever 14 such that, by means of rotational or pivoting movements of the lever 14, such a movement is transmitted to the valve inner drum 22. The circumference of the valve inner drum has an opening 24 and the circumference of the valve outer drum has an opening 25. In FIG. 3b, the valve is in a closed position, wherein the inner circumferential wall of the outer drum acts as a shut-off member in relation to the opening 24 of the valve inner drum. A cylindrical cavity which acts as a gas stream line is arranged in the interior of the valve inner drum 22. The dispensing line 8 is connected to said cavity.

Figure 4A:
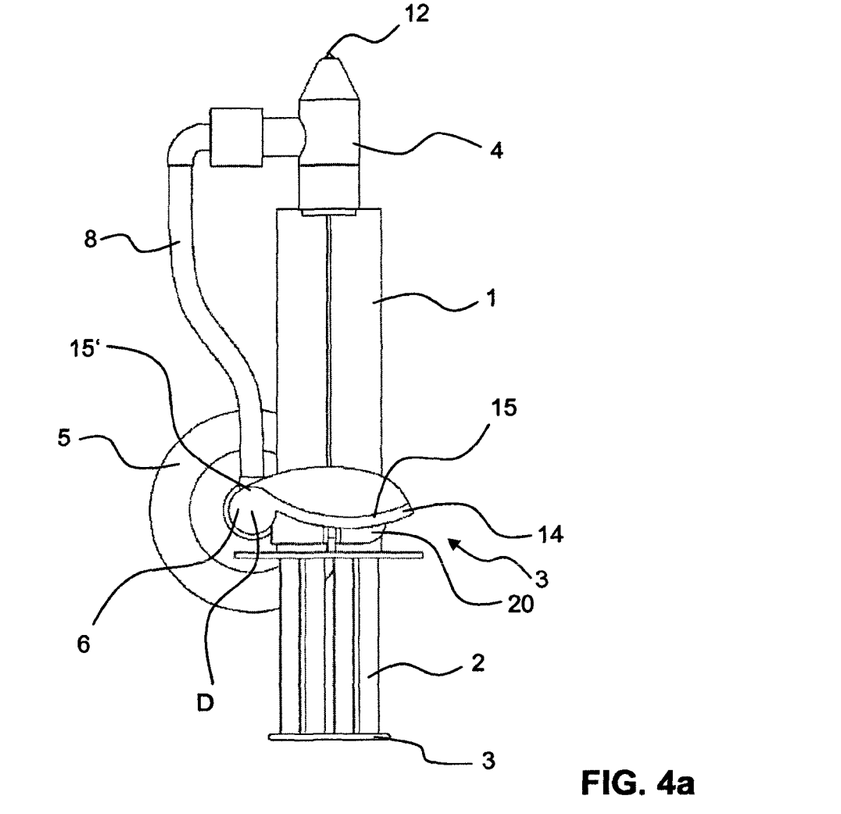

FIG. 4a shows the discharge apparatus in an actuating position, i.e. the valve of the compressed gas device is at least partially open such that compressed gas can flow out of the compressed gas source 5 through the valve 6 to the spray nozzle 4. The lever 14 of the counterpressure element 13 has been pivoted in the direction of the border of the container 1 and is therefore at a smaller distance from the border of the container 1 than in the inoperative position according to FIG. 3a.

Figure 4B:
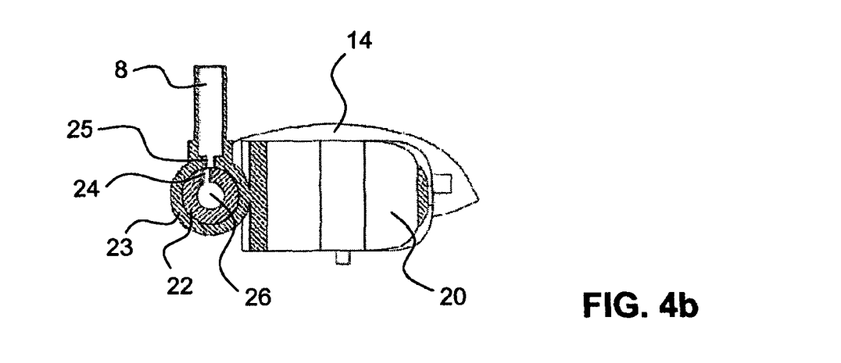
FIG. 4b shows a detailed longitudinal section through a valve of the discharge apparatus according to FIG. 4a, FIG. 5 shows a three-dimensional illustration of a subassembly with a counterpressure element according to the present invention.

As can be seen in FIG. 4b, the valve inner drum 22 has been rotated here together with the lever 14 within the valve outer drum 23 such that the opening 24 of the valve inner drum at least partially overlaps the opening 25 of the valve outer drum. A flow connection between the supply line 7 of the compressed gas source and the dispensing line 8 to the spray nozzle 4 is produced by said overlap.

In order to carry out a discharging of the components from the discharge apparatus, or a spraying of the components, a user grasps the discharge apparatus with one hand, for example from the left side as per FIGS. 3a and 4a. In the process, the container can come to lie between the index and middle fingers. The pressure surface 3 of the pressure element 2 can come to lie on the thumb. The index and middle fingers come to lie with the central region thereof on the counterpressure surface 15' in the region of the lever axis D while the fingertips rest on the counterpressure surface 15 along the lever arm. The user can now press together the fingers and the thumb, thus causing a force to be exerted on the pressure element 2 to advance the pressure element into the container 1 and onto the counterpressure element 13 or the counterpressure surface 15'. During the compression, the user can actuate the lever 14 by simultaneously pressing the fingertips down, and therefore the valve 6 is brought into an open position. Therefore, according to the present invention, at the same time as the pressure element 2 is advanced into the container 1 in order to discharge the components from the container 1, the compressed gas device can be actuated such that, as the components are discharged, a stream of compressed gas simultaneously emerges from the discharge opening.

As an alternative, it is also possible to grasp the discharge apparatus from the right side as per FIGS. 3a and 4a, with a user holding the discharge apparatus directly between the fingertips and the thumb. During this procedure, the force which is expended for advancing the pressure element 2 is also transmitted directly in the form of the counterpressure to the counterpressure surface 15 of the lever 14 of the counterpressure element 13. It is therefore not possible to release compressed gas for spraying the components from the discharge apparatus at too late a time or in too little an amount. In this embodiment, the movement for discharging the components is inseparably coupled to the movement for actuating the valve.

Figure 5:
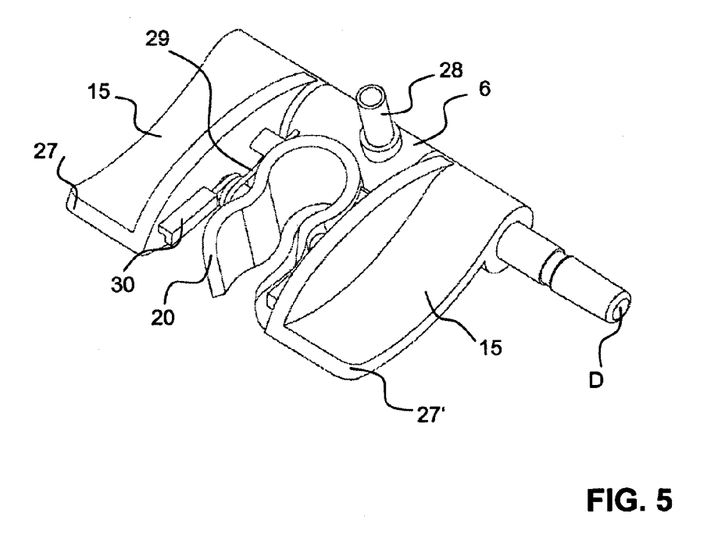
Figure 6:
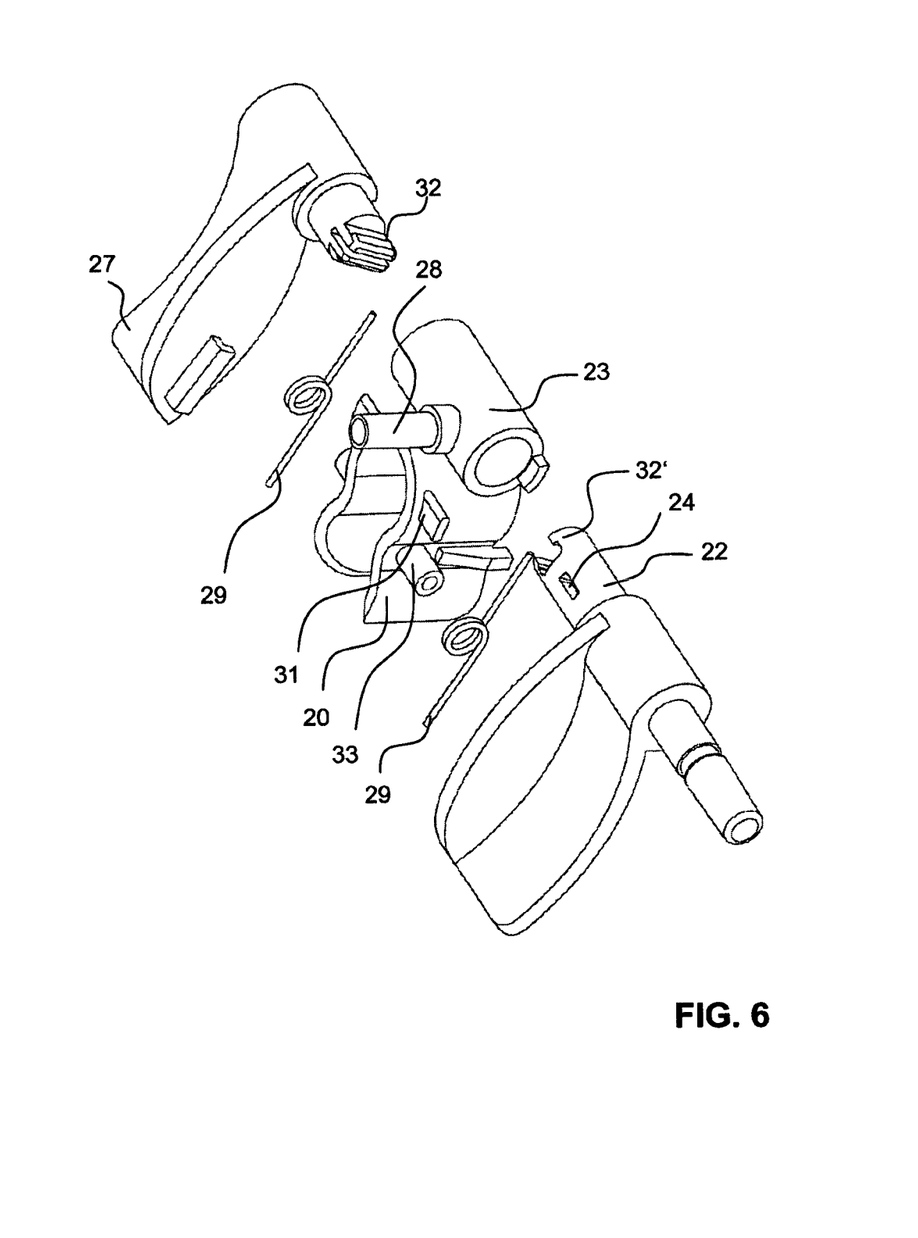
FIG. 6 shows an exploded view of the subassembly according to FIG. 5.

FIGS. 5 and 6 show a subassembly of the counterpressure element 13, which subassembly comprises the counterpressure element 13, the actuating device in the form of the lever 14, the valve 6, the supply and dispensing lines 7 and 8, the snap-on clip 20 and the springs 29. The snap-on clip 20 is designed corresponding to the form of the outer circumference of the container 3; in the present case, corresponding to the outer shape of a double syringe. Lever arms 27 of the lever 14 are shown on both sides next to the snap-on clip 20. The valve 6 with a dispensing nozzle 28 is shown between the lever arms 27. The lever arms 27 and the valve 6 are arranged along the axis of rotation of the lever. Springs 29 which serve to prestress the lever into an inoperative position are provided on both sides between the lever arms 27 and the snap-on clip 20. The lever 14 is pressed by said springs into a starting position of the discharge apparatus, in which the valve 6 is closed. The springs 29 are supported for this purpose with one end on a rail 30 on the lever arms 27 and with the other end on a holding projection 31 on the snap-on clip 20. When the lever is actuated, the lever arms 27 are pivoted relative to the snap-on clip 20 by pressure being applied to the counterpressure surfaces 15, and therefore the springs 29 are stretched further.

The first lever arm 27 has, along the axis D in the direction of the valve 6, a connecting device 32 with which said lever arm interacts with a connecting device 32' on the opposite second lever arm 27. The connecting devices 32 and 32' connect the lever arms fixedly to each other. The connection can be realized, for example, by means of a snap-on connection.

On the second lever arm 27, the valve inner drum 22 projects along the axis of rotation D in the direction of the first lever arm 27. The connecting device 32' is provided at the end of the valve inner drum 22. The valve outer drum 23 is manufactured as a separate component. The dispensing nozzle 28 protrudes from the outer circumference of the valve outer drum 23 over the opening 23 of the valve outer drum. On both sides next to the snap-on clip 20, the springs 29 are provided, which springs are mounted on a spring bearing 33 on the snap-on clip 20 and come to lie with the spring ends protruding in opposite directions between the rail 30 and the holding projections 31. In the assembled state, the connecting devices 32 and 32' and the valve inner drum 22 are plugged into the valve outer drum 23 and are connected unreleasably to each other within the valve outer drum such that, in the assembled state of the subassembly, the valve inner drum 22 comes to lie within the valve outer drum 23 and the two lever arms are prestressed by means of the springs 29 in a prestressed position relative to the snap-on clip 20, in which the opening 24 in the inner drum and the opening 25 in the outer drum do not overlap.

The subassembly of the counterpressure element 13 is depicted here as an independent constructional unit which can be placed onto a container. In principle, however, it is also possible, instead of the snap-on clip 20, to provide the individual structural elements of the subassembly directly on the container.

The invention has been described in FIGS. 1 to 6 with reference to an embodiment. In principle, however, variant embodiments and modifications of the inventive concept that go beyond the illustration in the drawings are possible. For example, instead of the rotary valve, a lifting valve can be provided for actuating the compressed gas device, as was explained at the beginning.

LIST OF REFERENCE NUMBERS

| | |
|---|---|
| 1 | Container, double syringe |
| 2 | Pressure element |
| 3 | Pressure surface |
| 4 | Spray nozzle |
| 5 | Compressed gas source |
| 6 | Valve |
| 7 | Supply line |
| 8 | Dispensing line |
| 9 | Holder |
| 10 | Snap-on arms |
| 11 | Gas inlet |
| 12 | Discharge opening |
| 13 | Counterpressure element |
| 14 | Lever |
| 15 | Counterpressure surface |
| 15' | Counterpressure surface |
| 16 | Openings |
| 17 | Component line |
| 18 | Compressed gas line |
| 19 | Cap nut |
| 20 | Snap-on clip |
| 21 | Projection |
| 22 | Valve inner drum |
| 23 | Valve outer drum |
| 24 | Opening (inner drum) |
| 25 | Opening (outer drum) |
| 26 | Cavity |
| 27 | Lever arms |
| 28 | Dispensing nozzle |
| 29 | Spring |
| 30 | Rail |
| 31 | Holding projection |
| 32, 32' | Connecting device |
| 33 | Spring bearing |

The invention claimed is:

1. A discharge apparatus for discharging a product and having compressed gas support, said discharge apparatus being designed so as, in its intended use, to be held and operated by means of one hand of a user, the discharge apparatus comprising:
a container for the product, with a discharge opening;
a pressure element which is mounted displaceably in the container and is designed so as, in its intended use, to be pressed into the container by the thumb of said hand;
a counterpressure element which is arranged on the container and, when a pressure is applied to the pressure element to advance the pressure element into the container, serves to absorb a counterpressure arising in the process, wherein the counterpressure element has at least one counterpressure surface which is arranged laterally on the container and is designed so as, in its intended use, to hold the container in a fixed position with at least one finger of the abovementioned hand while the pressure element is pressed into the container by the thumb;
a compressed gas device for dispensing compressed gas in the region of the discharge opening, with a valve for controlling the dispensing of the compressed gas; and
an actuating device for actuating the valve,
wherein the actuating device is arranged on the counterpressure element in such a manner that, in its intended use, the actuating device can be actuated with at least one finger of the abovementioned hand while at the same time the pressure element is pressed into the container by the thumb.

2. The discharge apparatus as claimed in claim 1, wherein the counterpressure element is removable from the container.

3. The discharge apparatus as claimed in claim 1, wherein the actuating device is prestressed by means of at least one spring in such a manner that the valve is in a closed position in an inoperative position of the actuating device and, when the actuating device is actuated, is movable into an at least partially open position counter to the force of the at least one spring.

4. The discharge apparatus as claimed in claim 1, wherein the counterpressure surface is formed on the actuating device and is movable by a counterpressure in such a manner that the valve can be actuated.

5. The discharge apparatus as claimed in claim 1, wherein an actuating surface for actuating the actuating device is formed next to the counterpressure surface, it being possible for an actuating pressure to be exerted on the actuating surface independently of the counterpressure on the counterpressure surface.

6. The discharge apparatus as claimed in claim 1, wherein the actuating device comprises at least one lever for actuating the valve.

7. The discharge apparatus as claimed in claim 6, wherein an axis of rotation of the lever is arranged substantially perpendicularly to the advancing direction of the pressure element.

8. The discharge apparatus as claimed in claim 6, wherein the counterpressure surface corresponds to a lever surface on a longitudinal side of the lever.

9. The discharge apparatus as claimed in claim 6, wherein the counterpressure surface is formed on a circumferential surface in the region of the axis of rotation of the lever, and wherein an actuating surface for actuating the lever is formed on the lever, it being possible for an actuating pressure to be exerted on the actuating surface independently of the counterpressure on the counterpressure surface.

10. The discharge apparatus as claimed in claim 1, wherein the valve is designed as a shut-off valve with a valve inner drum and a valve outer drum which are arranged concentrically with respect to each other and are rotatable with respect to each other.

11. The discharge apparatus as claimed in claim 10, wherein the actuating device comprises at least one lever for actuating the valve, and wherein the valve inner drum is stationary relative to the lever and the valve outer drum is stationary relative to the container.

12. The discharge apparatus as claimed in claim 10, wherein the actuating device comprises at least one lever for actuating the valve, and wherein the axis of the valve inner drum and of the valve outer drum corresponds to the axis of rotation of the lever.

13. A method for discharging a product from a discharge apparatus with compressed gas support, said discharge apparatus being designed so as, in its intended use, to be held and operated by means of one hand of a user, the discharge apparatus comprising:
a container for the product, with a discharge opening;
a pressure element which is mounted displaceably in the container and is designed so as to be pressed into the container by the thumb of said hand;

a counterpressure element which is arranged on the container and, when a pressure is applied to the pressure element to advance the pressure element into the container, serves to absorb a counterpressure arising in the process, wherein the counterpressure element has at least one counterpressure surface which is arranged laterally on the container and is designed so as, in its intended use, to hold the container in a fixed position with at least one finger of the abovementioned hand while the pressure element is pressed into the container by the thumb;

a compressed gas device for dispensing compressed gas in the region of the discharge opening, with a valve for controlling the dispensing of the compressed gas; and an actuating device for actuating the valve, wherein the actuating device is arranged on the counterpressure element in such a manner that, in its intended use, the actuating device can be actuated with at least one finger of the abovementioned hand while at the same time the pressure element is pressed into the container by the thumb, wherein the method comprises the following steps:

grasping the discharge apparatus with one hand, wherein the thumb comes to lie on the pressure element and at least one finger comes to lie on the counterpressure element; and compressing the pressure and counterpressure elements with the thumb and at least one finger, the pressure element being advanced into the container and the actuating device being actuated simultaneously.

* * * * *